United States Patent [19]

Pomparelli

[11] Patent Number: 4,880,420
[45] Date of Patent: * Nov. 14, 1989

[54] MULTIPLE STRAND ELASTIC MEANS

[75] Inventor: Vincent Pomparelli, Parlin, N.J.

[73] Assignee: McNeil-PPC, Inc., Milltown, N.J.

[ * ] Notice: The portion of the term of this patent subsequent to Feb. 14, 2004 has been disclaimed.

[21] Appl. No.: 641,665

[22] Filed: Aug. 17, 1984

[51] Int. Cl.⁴ ............................................. A61F 13/16
[52] U.S. Cl. .................................................. 604/385.1
[58] Field of Search .................... 604/385, 366, 370

[56] References Cited

U.S. PATENT DOCUMENTS

| | | | |
|---|---|---|---|
| 4,081,301 | 3/1978 | Buell | 156/164 |
| 4,325,372 | 4/1982 | Teed | 604/385.2 |
| 4,430,086 | 2/1984 | Repke | 604/385.2 |
| 4,450,026 | 5/1984 | Pieniak et al. | 604/385.2 |

Primary Examiner—C. Fred Rosenbaum
Attorney, Agent, or Firm—Robert L. Minier

[57] ABSTRACT

An elastic means is provided for a disposable diaper which elastic means has substantially parallel multiple strands of stretched elastic adhered between two layers of fabric by at least one sinusoidal adhesive line.

3 Claims, 2 Drawing Sheets

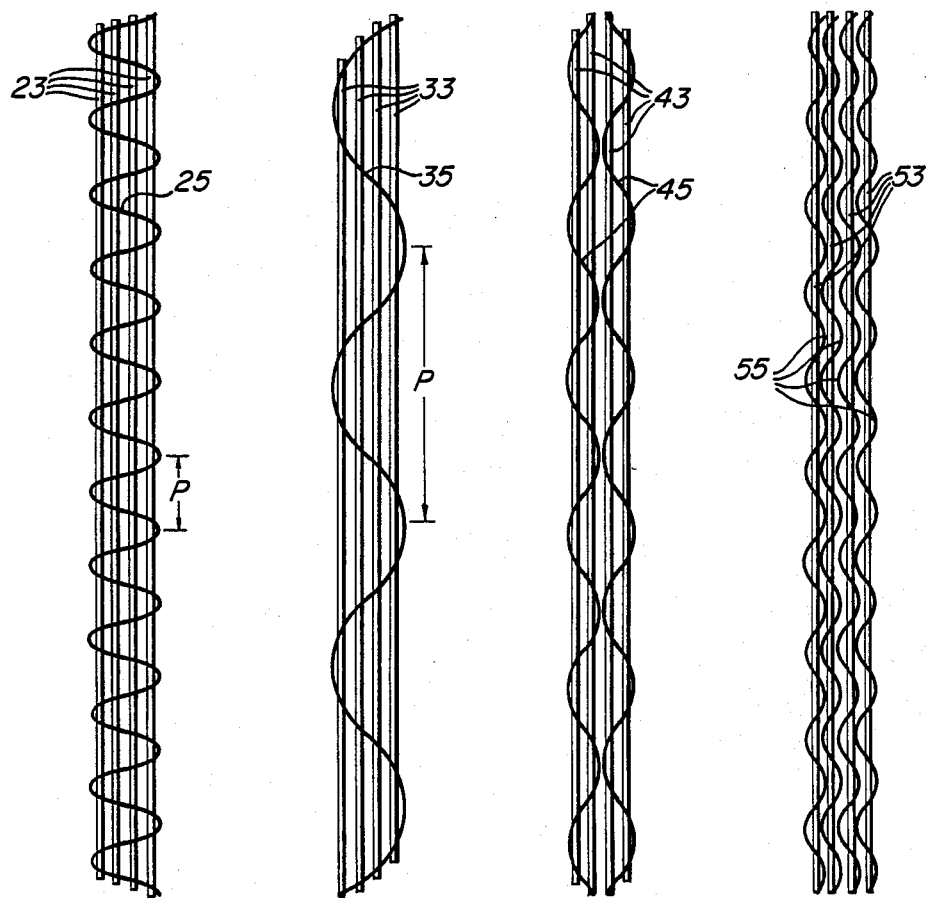

MULTIPLE STRAND ELASTIC MEANS

BACKGROUND OF THE INVENTION

The present invention relates to a new and improved multiple strand elastic means. More particularly, the present invention relates to a means for adhering multiple strands of elastic in a product such as a disposable diaper product.

Disposable diaper products have been known for some time. A disposable diaper product generally consists of a liquid-impermeable backing sheet, a liquid-permeable facing sheet, and an absorbent core laminated between the facing and backing sheets. Initially, in many of these products the absorbent core consisted of "wadding" or plies of tissue. Diapers utilizing such an absorbent core are disclosed in U.S. Pat. No. Re. 26,151.

The wadding type of batt or core was replaced for the most part by an improved absorbent batt which generally comprises what is termed "fluffed wood pulp fibers". This absorbent batt which is a layer of individualized wood pulp fibers has substantial thickness. A diaper which incorporates such a fluffed wood pulp absorbent batt is described in U.S. Pat. No. 2,788,003. This diaper had improved absorbent capacity and somewhat better containment than a diaper using a wadding layer. Also, the fluffed wood pulp layer is quite soft, flexible, and conformable, and hence produces an improved diaper as to the feeling and softness.

Even though the fluffed wood pulp absorbent batts improve the capacity of the disposable diaper, they remain quite thick. Such thickness provides a problem with respect to containment of the liquid, and thus, the clothes of the infant may become wet and/or stained.

One answer for leaking diapers provided in the marketplace has been the elastic-leg diapers or stretch diapers. Though these diapers provide no better absorbent batt than previous diapers, they have indicated improved containment of liquid. Such diapers are disclosed and described in U.S. Pat. Nos. 3,860,003; 4,050,462; 4,324,245; and 4,430,086. Though the containment features are better than the prior art products, the elasticized products of these patents and those in the marketplace at the present time fit more tightly permitting less air circulation. Frequently, this can become irritating to the skin and the tighter the elastic or the more close fitting the diaper, the greater the irritation. This is especially true adjacent the area where the elastic leg portion of the product contacts the wearer.

Furthermore, the adherence of the elastic to the backing, or facing, or both, has been a problem in the art. For instance, U.S. Pat. No. 4,081,301 attempts to solve the problem of adhering elastic by intermittently applying adhesive to the elastic, adhering the elastic member to the facing or the backing of a disposable diaper product, and then severing the elastic in the unadhered portion. In this method and others known similar to it, it has been deemed necessary to provide adhesive along substantially the entire length of the elastic member where it is desirable to adhere the elastic. The addition of adhesive along the stretched portion of the elastic provides an additional thickness to the elastic and at least partially interferes with the gathering power of the elastic member.

The present invention provides a new and improved means for adhering multiple strands of elastic in a disposable diaper product. The new means of adhering the elastic saves a large amount of adhesive, provides a very soft gathering zone, provides uniformity in the gathering of the elastic member, and couples the motion of the surrounding fabric to the elastic. Furthermore, it is particularly suitable for providing breathability in the elastic zone.

SUMMARY OF THE INVENTION

The present invention provides an elastic means for a disposable diaper which comprises multiple, substantially parallel strands of stretched elastic, which strands are adhered to at least one fabric and preferably between two layers of fabric by at least one sinusoidal adhesive line. It has been discovered that multiple strands of elastic in a disposable diaper product to gather the leg band area are preferable to a single strand of elastic. To adhere each strand its entire length provides the disadvantages discussed heretofore. It has been discovered that the use of a single sinusoidal adhesive line provides a highly desirable result. A sinusoidal adhesive line is one which is wavy, or undulates, and is not a straight line of adhesive. The sinusoidal adhesive line may adhere more than one elastic strand or each elastic strand may have its own sinusoidal adhesive line. In either case, the advantages mentioned heretofore are achieved.

BRIEF DESCRIPTION OF THE DRAWINGS

FIG. 2 is a plan view of one embodiment of the present invention;

FIG. 3 is a plan view of another embodiment of the present invention;

FIG. 4 is a plan view of a further embodiment of the present invention; and

FIG. 5 is a plan view of a still further embodiment of the present invention.

DETAILED DESCRIPTION OF THE INVENTION

Figure 1:
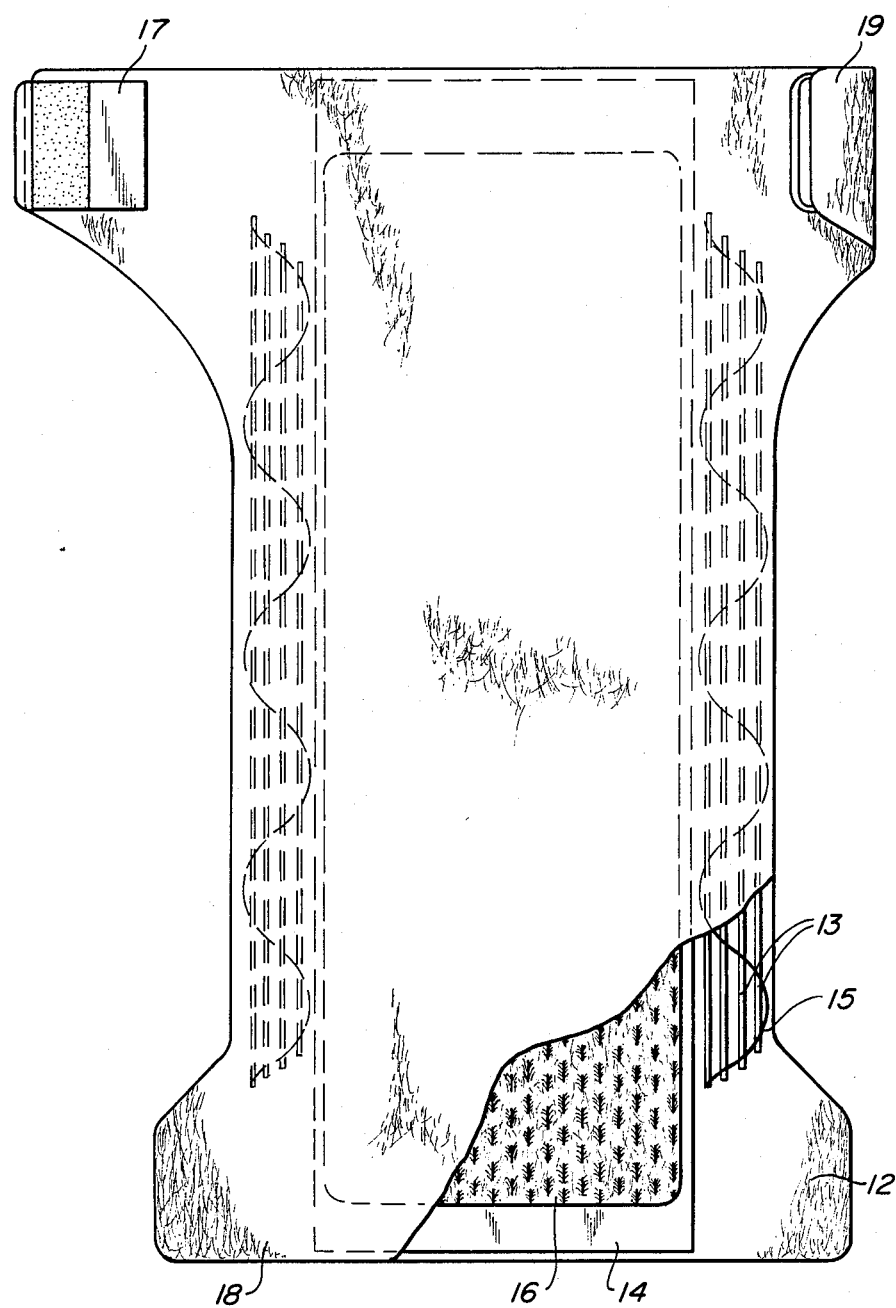
FIG. 1 is a plan view of a disposable diaper exhibiting one embodiment of the present invention, especially shown in the portion broken away for clarity.

Referring to FIG. 1, a disposable diaper 10 is shown. The diaper has a backing sheet 12 and a facing sheet 18. The backing and facing sheets extend beyond the absorbent core which in this case consists of a liquid barrier 14 and an absorbent core 16. In the broken away portion of the drawing, it can be seen that the elastic strands 13 are held in place by the sinusoidal adhesive line 15. In this instance, the sinusoidal line 15 is placed on the backing sheet 12 and the elastic strands placed on top of the glue line after which the facing sheet 18 is adhered to the backing sheet by the portions of the sinusoidal adhesive line which are not beneath the elastic strands. In this manner, the adhesive line serves a dual purpose, i.e., to adhere the elastic strands to the backing sheet 12 and to adhere the facing sheet 18 to the backing sheet as well. Tape tabs 17 and 19 are affixed in each corner of the diaper product at the back waist line to secure the diaper product about the body of the infant.

FIG. 2 depicts strands of elastic 23 adhered to a desirable substrate by a sinusoidal adhesive line 25. The "pitch" of a sinusoidal line is the distance between two adjacent peaks of the line. In FIG. 2, the pitch is denoted by "p". In the instance in FIG. 2, the pitch might be as low as 0.3 inch.

FIG. 3 depicts a sinusoidal adhesive line 35 suitable for adhering elastic strands 33 which has a pitch which may be as high as 1.5 inch or more.

FIG. 4 shows two sinusoidal lines 45 used to adhere multiple elastic strands 43. In this instance each of the lines 45 attaches two strands of elastic.

FIG. 5 depicts the situation wherein a sinusoidal adhesive line 55 is used on each strand of elastic 53 that is to be adhered.

The elastic means provided by the present invention provides a soft, gathering region at the leg band or if desired the waist band of a disposable diaper product. It has been noted that when the elastic means of the present invention is used, there are substantially no red lines depicting irritation made on the skin of the infant wearing the disposable diaper product. It is also noted that the gathering provided by the elastic means is uniform and couples the motion of the surrounding fabric to the elastic. This provides for a more complete gasket about the leg of the infant without the disadvantage of creating lines in the infant's skin. The gathering pattern provided by the elastic means of the present invention is changed from that normally seen in other commercial products such that more of the fabric is in contact with the infant's skin thus providing both a better gasket and a softer gasket without marking the skin of the infant. Because the gasket is formed by fabric instead of elastic, the leg band is much more breathable.

The elastic means of the present invention is preferably placed between two layers of fabric in the margins of a disposable diaper product. The term "fabric" is used herein to include fabrics, whether they be woven or nonwoven, films, whether they be continuous or breathable, netting, scrims, and the like.

It had been found in order to satisfactorily adhere four single strands of elastic in the leg band of a disposable diaper product, it was necessary to adhere the elastic strands at each end by use of a mass of adhesive going across the space between the strands as well as encompassing the strands, which mass of adhesive needed to be at least a ¼ inch in width. It was then observed in order to retain a sufficient amount of the elastic power of each strand, it was better not to adhere the strand's entire length but rather to place adhesive on each side of the strand to adhere the backing and facing together thereby providing channels within which the elastic would lie. By use of this method, the strands were held sufficiently in place that a gathering effect was achieved. In order to adequately secure four strands of elastic which are approximately 0.032 inch in width and are extended 100 percent, it is found necessary to use 0.655 grams of hot melt adhesive per diaper. Four strands of elastic are held in place by using an adhesive mask at the end of the elastic strands which is about ½ inch by ¼ inch, and five adhesive lines between the elastic bands to provide the channels within which the elastic bands would lie.

In the present invention, the elastic strands, generally not more than ¼ inch in width, may be placed close together, i.e., about 0.032 inch apart up to about ¼ inch or ½ inch or more apart.

The sinusoidal glue line extends at least about 1/16 inch up to about ½ inch or more beyond the outside elastic strand. This extension assures adherence of the facing to the backing just outside the outermost elastic strand.

A comparative example of the diaper of the present invention to the product just discussed above is as follows. This example is not intended to be limiting in any way and extensions and modifications thereof without departure from the spirit and scope of the invention will become apparent from this example.

EXAMPLE

In this example, hot melt adhesive manufactured by Findley Adhesives and identified as Product No. 691-336 is used. Any suitable adhesive can be used in the present invention. A diaper product, approximately 18 inches in length, is made in accordance with that shown in FIG. 1. The elastic elements, four on each side of the absorbent core, are each 11 ½ inches in length. The elastic strands in their relaxed state are approximately 5 ¾ inches in length. In this example, 0.003 grams per inch of adhesive line are placed in a sinusoidal pattern wherein four lines are used as shown in FIG. 5. The lines have a pitch of approximately 0.6 inch and have a ⅛ inch pattern width. The amount of adhesive required for each diaper is 0.313 gram. This is true in spite of the fact that 8 lines of adhesive extending at least 11.5 inches have been provided.

In the instance wherein one sinusoidal line is used to adhere two strands of elastic in place and each line has a pitch of ½ inch, approximately 0.224 grams per diaper of adhesive is used. Wherein a single sinusoidal line of adhesive for each four strands of elastic is used in the diaper and the glue line has a one inch pitch, the amount of adhesive used is approximately 0.128 gram per diaper.

It can be seen from the above that the use of sinusoidal lines to adhere multiple strands of elastic in a diaper product requires considerably less adhesive as well as gaining all of the other advantages heretofore disclosed. Furthermore, the sinusoidal type glue line permits use of a very fine or narrow glue line because the two layers of fabric immediately adjacent the elastic are adhered to each other.

From the foregoing it will be observed that numerous variations and modifications may be effected without departing from the true spirit and scope of the novel concept of this invention.

I claim:

1. In a disposable diaper having elastic leg portions, said diaper comprising a liquid impermeable backing sheet, a liquid permeable facing sheet and an absorbent core disposed between said facing sheet and said backing sheet, the improvement comprising said elastic leg portions being formed by a multiplicity of substantially parallel unconnected strands of stretched elastic adhered between the facing sheet and the backing sheet by at least one continuous sinusoidal adhesive line, said adhesive line extending beyond at least one elastic strand on each side of said strand as well as across said strand and said adhesive line adhering not only at least one elastic strand but also adhering said facing layer to said backing layer.

2. The disposable diaper of claim 1 wherein said sinusoidal adhesive line adheres more than one unconnected strand of elastic.

3. The disposable diaper of claim 1 wherein more than one continuous sinusoidal adhesive line is provided with each line adhering at least one unconnected elastic strand between said facing layer and said backing layer.

* * * * *